United States Patent
Paetzold

(10) Patent No.: US 10,246,673 B2
(45) Date of Patent: Apr. 2, 2019

(54) USE OF LIGNIFIED STALKS OR OF AT LEAST ONE EXTRACT OF LIGNIFIED STALKS IN A COSMETIC COMPOSITION, A FOOD SUPPLEMENT, A NUTRITIONAL PRODUCT, A FOOD OR A BEVERAGE

(71) Applicant: Michael Paetzold, La Brede (FR)

(72) Inventor: Michael Paetzold, La Brede (FR)

( * ) Notice: Subject to any disclaimer, the term of this patent is extended or adjusted under 35 U.S.C. 154(b) by 157 days.

(21) Appl. No.: 15/127,713

(22) PCT Filed: Mar. 21, 2014

(86) PCT No.: PCT/FR2014/050664
§ 371 (c)(1),
(2) Date: Sep. 20, 2016

(87) PCT Pub. No.: WO2015/140419
PCT Pub. Date: Sep. 24, 2015

(65) Prior Publication Data
US 2017/0137761 A1 May 18, 2017

(51) Int. Cl.
| | |
|---|---|
| *A23L 2/56* | (2006.01) |
| *C12H 1/22* | (2006.01) |
| *A61K 36/87* | (2006.01) |
| *A61K 8/97* | (2017.01) |
| *C12F 3/06* | (2006.01) |
| *C12C 5/02* | (2006.01) |
| *A61Q 19/00* | (2006.01) |

(52) U.S. Cl.
CPC .................. *C12H 1/22* (2013.01); *A23L 2/56* (2013.01); *A61K 8/97* (2013.01); *A61K 36/87* (2013.01); *A61Q 19/00* (2013.01); *C12C 5/026* (2013.01); *C12F 3/06* (2013.01); *A23V 2002/00* (2013.01); *A61K 2236/00* (2013.01); *C12G 2200/21* (2013.01)

(58) Field of Classification Search
CPC ............ C12H 1/22; C12C 5/026; A23L 2/561
USPC ..................... 426/590, 11, 12, 650, 615, 425
See application file for complete search history.

(56) References Cited

U.S. PATENT DOCUMENTS

2009/0092695 A1 4/2009 Chen et al.
2011/0020498 A1* 1/2011 Broekaert et al.

FOREIGN PATENT DOCUMENTS

CN 103525610 A 1/2014

OTHER PUBLICATIONS

Parts of the Grape Vine:Shoots, May 21, 2018, http://articles.extension.org/pages31098/parts-of-the-grape-vine:-shoots, pp. 1-5.*
B. Piermattei, et al., Preliminary studies on the use of dried grape stems in red winemaking, Rivista di Viticoltura e di Enologia, 1999 (abstract only).
Becca, Grape Stem Extracts: An Example of Utilizing Winery Waste for a More Sustainable Industry, The Academic Wino, Nov. 5, 2012, pp. 1-3.
Sierra Rayne, et al., Grape cane waste as a source of trans-resveratrol and trans-viniferin: High-value phytochemicals with medicinal and anti-phytopathogenic applications, Industrial Crops and Products, 2008, pp. 335-340, vol. 27, Elsevier B.V.
Maria Anastasiadi, et al., Grape stem extracts: Polyphenolic content and assessment of their in vitro antioxidant properties, LWT—Food Science and Technology, 2012, pp. 316-322, vol. 48, Elsevier Ltd.
Lan Ping, et al., Evaluation of grape stalks as a bioresource, Industrial Crops and Products, 2011, pp. 200-204, vol. 33, Elsevier B.V.
Eder C. Lima, et al., Adsorption of Cu(II) on Araucaria angustifolia wastes: Determination of the optimal conditions by statistic design of experiment, Journal of Hazardous Materials, 2007, pp. 211-220, vol. 140, Elsevier B.V.
Mar. 12, 2014, International Search Report issued for International Application No. PCT/FR2014/050664.

* cited by examiner

*Primary Examiner* — Helen F Heggestad
(74) *Attorney, Agent, or Firm* — Young & Thompson

(57) ABSTRACT

Disclosed is the use of lignified stalks, of at least one extract of lignified stalks or of a composition containing same in a cosmetic composition, a food supplement, a nutritional product, a food or a beverage.

20 Claims, No Drawings

USE OF LIGNIFIED STALKS OR OF AT LEAST ONE EXTRACT OF LIGNIFIED STALKS IN A COSMETIC COMPOSITION, A FOOD SUPPLEMENT, A NUTRITIONAL PRODUCT, A FOOD OR A BEVERAGE

This invention relates to a use of lignified stalks or of at least one extract of lignified stalks in a cosmetic composition, a food supplement, a nutritional product, a food, or a beverage. The invention also relates to ground lignified stalks, an extract of lignified stalks, or a composition containing it.

In the case of a red wine, a wine-making method comprises the following stages:

The more or less destalked and crushed harvest is put into a fermentation vat. The destalking operation consists in separating the excess stems and stalks. These ligneous parts generally create herbaceous tastes during a long fermentation in vats. During the fermentation in vats, an alcoholic fermentation and an extraction are performed. During this phase, the solids (pulp, skin, . . . . ) rise to the surface and float on the juice. This mass of solids is called a hat. The juice is pumped at regular intervals to the bottom of the vat to be spread on the hat so as to promote extraction. At the end of the alcoholic fermentation phase, the draining-off of the vat is initiated so as to recover the juice, called "free-run wine." The solids that have remained at the bottom of the vat are called the pulp. The latter is removed from the vat to be pressed in such a way as to obtain the press wine. The remaining dry and compacted pulp is definitively separated from the wine. It can be used for composting.

Next, the wine can be subjected to a malolactic fermentation phase.

At the end of this last fermentation, the wine is put into barrels and allowed to rise there for several months before being bottled. During this period, the fine particles in suspension in the wine settle gently at the bottoms of the barrels to form sediment. Only the liquid part (top of the barrel) will be bottled.

The free-run wine and the press wine are generally raised separately and can be subsequently assembled based on the organoleptic properties of each one.

When the structure of the wine justifies it, the aging of the wine is done in wooden barrels so as to enhance the structure of the wine by providing external tannins obtained from the wood of the barrel and to develop the wine's aromas.

According to other wine-aging techniques, wine can be stored in inert vats into which wood chips are put. As a variant, the wood chips can be introduced during wine-making, for example during alcoholic fermentation.

The input of wood (barrels or chips) depends on the essence of the wood and the heat to which the wood is subjected.

With the wood that is used generally being oak, the aromatic and gustatory inputs are thereby closely linked to the heating of the wood.

Finally, the assembly technique makes it possible to mix multiple vats, originating from, for example, different plots on a property, of free-run wine or press wine so as to produce a wine.

According to other techniques described in publications, after the destalking phase, it is possible to treat the stalks that are "green" (or in the vegetable state) with vapor so as to extract certain components. However, this solution is not preferred because in the vegetable state, the stalks release components that have a tendency to produce wine with an herbaceous or bitter taste.

In the wine-making field, the "green" stalks and the grape pulp that contain the skin and the grape seed pips are considered to be waste.

In the cosmetic field, it is known to use pips or skins of grapes to extract therefrom certain components so as to obtain an active ingredient.

However, the stalks that are "green" or in the vegetable state are considered to be waste, and are optionally upgraded as an organic soil conditioner.

The invention proposes another solution for upgrading the stalks that are "green" or in the vegetable state.

For this purpose, the invention has as its object the use of lignified stalks, of at least one extract of lignified stalks, or of a composition containing it in a cosmetic composition, a food supplement, a nutritional product, a food, or a beverage.

For this application, stalk is defined both as the entire stalk as well as stalk pieces.

Hereinafter, lignified is defined as a state of stalks in which they have taken on the appearance of wood, with the stalks being green and having the appearance of a vegetable at harvest time and brown in the lignified state. Thus, the lignification is a process by which the membranes of certain vegetable cells are transformed, under the action of the lignin, into wood.

Thus, according to the invention, the stalks go through a lignification phase to remove herbaceous and bitter tastes before being put into the wine.

Advantageously, the stalks are dried to accelerate the lignification. This drying can be done naturally or artificially. In a natural manner, the drying lasts on the order of 3 to 5 weeks to achieve the lignification of the stalks.

At the end of the harvest, the stalk comprises a peduncle, pedicels, and little bulges called brushes that are located at the ends of the pedicels at the points where the seeds are attached.

Advantageously, after the lignification phase, the stalks go through a sorting stage whose purpose is to remove the little bulges or brushes, which have a tendency to become detached from the rest of the stalk after drying.

Preferably, the sorting makes it possible to preserve only the surface parts of the stalks or stalk pieces. Surface part is defined as the skin, the bark, or the ligneous part of the stalks if the latter are only partially lignified.

According to a first variant, after the lignification phase and at the end of the possible sorting operation, the stalks are cut into homogeneous pieces.

According to a preferred embodiment, the stalks that are lignified and preferably sorted and cut are subjected to a heating stage in the manner of the wood of a cask. For this purpose, the lignified stalks are roasted or toasted. This stage makes it possible to be able to modulate the olfactory and gustatory properties of the stalks based on the temperature and duration of heating.

According to another variant, after the lignification phase and after the optional sorting operation, the lignified stalks are ground. Advantageously, the grain size of the lignified stalk powder obtained after grinding is to be less than 0.5 mm.

Lignified stalks in powder form are defined as the ground material obtained by the grinding of lignified stalks or a fraction of the ground material.

This variant makes it possible to obtain a better extraction of the components that originate from the lignified stalks.

Prior to the grinding stage or optionally subsequently, the lignified stalks that may or may not be ground are subjected to a heating stage in the manner of the wood of a cask. For this purpose, the lignified stalks that may or may not be ground are roasted or toasted. This stage makes it possible to be able to modulate the olfactory and gustatory properties of the stalks based on the temperature and duration of heating.

The invention also proposes a device for producing lignified stalks. This device comprises a preferably continuous furnace. Thus, the stalks that are advantageously cut and sorted pass under the heating means.

According to an embodiment, the device comprises one station ensuring the cutting of stalks and another station for sorting the cut stalks and removing the little bulges located at the ends of the pedicels, for example a sieve. At the end of this sorting, the cut and sorted stalks are arranged on a conveyor that passes through a furnace. The furnace can also ensure the roasting of the cut and sorted stalks.

The invention also proposes a product or a composition that comprises lignified stalks that are whole, in pieces, or in powder form.

According to one packaging mode, the product exclusively contains lignified stalks that are whole, in pieces, or in powder form.

According to another packaging mode, the product comprises an aqueous phase that contains lignified stalks that are whole, in pieces, or in powder form.

According to another packaging mode, the lignified stalks that are whole, in pieces, or in powder form are packaged in dry form in a permeable container. In this case, the invention proposes a product that comprises a permeable container that contains lignified stalks that are whole, in pieces, or in powder form.

Permeable container is defined as at least one portion of the wall of the container being permeable to the liquid while retaining the lignified stalks that are whole, in pieces, or in powder form. This solution makes it possible to be able to remove all of the elements of the lignified stalks that are put into a liquid at the end of a phase of extraction, maceration, and infusion.

According to an embodiment, the container is a bag, such as an infusion bag, for example.

The invention also proposes an extract of lignified stalks or of a composition comprising at least one extract of lignified stalks. The lignified stalk extract can be obtained from lignified stalks, optionally sorted and/or roasted and/or toasted.

According to a first variant, the lignified stalk extract is obtained by a method comprising at least one aqueous extraction stage.

Preferably, the aqueous extraction method comprises at least one stage for solubilization of lignified stalks in water or in a mixture of water and alcohol.

Advantageously, the aqueous extraction method comprises at least one infusion stage.

In a simplified manner, the aqueous extraction can consist in macerating lignified stalks that are whole, in pieces, or in powder form into a liquid, with the lignified stalks that are whole, in pieces, or in powder form being removed from the liquid after a certain duration.

According to a second variant, the lignified stalk extract is obtained by a method comprising at least one stage for hydrolysis of lignified stalks. This hydrolysis can be an acid or base hydrolysis or an enzymatic hydrolysis.

The above-cited products based on lignified stalks are rich in polyphenols, in particular in resveratrol, in melatonin, in tannins, in aromas, . . . .

The above-cited products based on lignified stalks will have organoleptic characteristics that will be different based on the variety of grape from which the stalks are obtained.

According to a first use, the lignified stalks are used in a method of wine-making or wine-aging.

According to a first operating mode, the wine-making or wine-aging method comprises a stage that consists in macerating in the wine lignified stalks that are whole, in pieces, or in powder form.

The maceration of the stalks can be done equally well during different phases of the development of the wine, for example when the harvest is put into a vat.

Preferably, the addition of lignified stalks is done at the end of the fermentation phases during the phase of aging the wine. The maceration of the lignified stalks can be controlled in a more precise manner during this phase.

According to a first variant, after the operation of destalking or pressing, the stalks are preserved. They are dried naturally in such a way as to achieve the lignification of the stalks. They are preferably used for the next harvests. Thus, according to this operating mode, the lignified stalks put into the wine are not those that supported the grape seeds from which wine is produced.

According to another variant, after the destalking or pressing operation, the stalks are lignified by drying naturally. After a duration on the order of 1 to 5 weeks, they are put into the wine that is produced from grape seeds carried by the lignified stalks.

According to another variant, after the destalking or pressing operation, the stalks are lignified using a furnace that can also ensure the roasting. Thus, according to this operating mode, the lignified stalks put into the wine are those that supported the grape seeds from which wine is produced.

According to a characteristic of the invention, the metering of the product or the composition comprising lignified stalks that are whole, in pieces, or in powder form put into the wine is between 1 gr/hl and 10 gr/hl.

The duration of maceration of the lignified stalks as well as their quantities are adjusted based on the olfactory and gustatory properties that are desired.

According to a second operating mode, the method for wine-making and wine-aging comprises a stage that consists in putting into the wine a product or a composition comprising lignified stalk powder, a lignified stalk extract, or an aqueous phase in which lignified stalks that are whole, in pieces, or in powder form have been macerated or infused.

The advantages of the wine-making method whose purpose is to macerate the lignified stalks in wine are as follows:

In the first place, this solution makes it possible to upgrade a component of the harvest, namely the stalks, whose olfactory and gustatory characteristics have not been exploited. In contrast, the non-lignified stalks had a tendency to be removed during the destalking so as not to impart to the wine an herbaceous or bitter taste.

In the second place, it makes possible an input with olfactory and gustatory nuances not heretofore exploited that complete the panel of the organoleptic properties of a wine. Thus, it is possible to adjust the input based on the nature of the grape variety and the soil of the stalks, based on the drying of the stalks, and based on the heating of the stalks.

The lignified stalks can be used for other applications.

According to another application, the invention proposes the use of lignified stalks that are whole, in pieces, or in powder form, of at least one lignified stalk extract, or of a composition containing it as an active ingredient in a cosmetic composition. The cosmetic compositions that are thus obtained, rich in polyphenols, are more particularly intended for skin care.

According to another application, the invention proposes the use of lignified stalks that are whole, in pieces, or in powder form of at least one lignified stalk extract or of a composition containing it as a nutritional active ingredient in a food supplement or a nutritional product.

According to another application, the invention proposes the use of lignified stalks that are whole, in pieces, or in powder form of at least one lignified stalk extract or of a composition containing it as an enhancer, a flavoring agent, or an aromatizing agent in beverages or food.

Thus, it is possible to aromatize a beer with a lignified stalk extract. For this beverage, the lignified stalk extract is used for its tannins, its aromas, its sweetness, and as an enhancer. By way of example, beer is aromatized into merlot by adding to the beer a lignified stalk extract obtained from merlot clusters.

It is also possible to produce a soft drink having aromas and taste close to those of wine by incorporating a lignified stalk extract into said soft drink.

The invention claimed is:

1. A method for enhancing a flavor or an aroma of a beverage, comprising the steps of:
   lignifying stalks for 1 to 5 weeks, during which membranes of certain plant cells of the stalks are transformed, under the action of the lignin, into wood, to obtain lignified stalks; and
   adding to a beverage at least one lignified stalk extract obtained from the lignified stalks in which lignified stalks are whole, in pieces, or in powder form, or a composition containing the at least one lignified stalk extract, as a flavoring agent or an aromatizing agent to enhance a flavor or an aroma of said beverage.

2. The method according to claim 1, further comprising subjecting the lignified stalks obtained from the lignifying step to aqueous extraction to obtain the at least one lignified stalk extract.

3. The method according to claim 2, wherein the aqueous extraction comprises solubilizing the lignified stalks obtained from the lignifying step in water.

4. The method according to claim 3, wherein the aqueous extraction comprises infusing the lignified stalks.

5. The method according to claim 3, wherein the obtained from the lignifying step lignified stalks are ground.

6. The method according to claim 2, wherein the aqueous extraction comprises solubilizing the lignified stalks obtained from the lignifying step in a mixture of water and alcohol.

7. The method according to claim 6, wherein the aqueous extraction comprises infusing the lignified stalks.

8. The method according to claim 6, wherein the lignified stalks obtained from the lignifying step are ground.

9. The method according to claim 2, wherein the aqueous extraction comprises infusing the lignified stalks.

10. The method according to claim 9, wherein the lignified stalks obtained from the lignifying step are ground.

11. The method according to claim 2, wherein the lignified stalks obtained from the lignifying step are ground.

12. A beverage obtained from the method according to claim 2.

13. The method according to claim 1, further comprising hydrolyzing the lignified stalks obtained from the lignifying step to obtain the at least one liquid stalk extract.

14. The method according to claim 13, wherein the hydrolysis is an acid or base hydrolysis.

15. The method according to claim 14, wherein the lignified stalks obtained from the lignifying step are ground.

16. The method according to claim 13, wherein the hydrolysis is an enzymatic hydrolysis.

17. The method according to claim 16, wherein the lignified stalks obtained from the lignifying step are ground.

18. The method according to claim 13, wherein the lignified stalks obtained from the lignifying step are ground.

19. The method according to claim 1, wherein the lignified stalks obtained from the lignifying step are ground.

20. A beverage obtained from the method according to claim 1.

* * * * *